US012094585B2

(12) United States Patent
Hagenbrock et al.

(10) Patent No.: US 12,094,585 B2
(45) Date of Patent: Sep. 17, 2024

(54) REAL-TIME ECG REPORT GENERATION

(71) Applicant: Preventice Solutions, Inc., Rochester, MN (US)

(72) Inventors: Jan Hagenbrock, Rochester, MN (US); David Engebretsen, Eagan, MN (US); David Will, Rochester, MN (US); Riley Ellis, Rochester, MN (US); Jake Matras, Eagan, MN (US); Tim McClanahan, Rochester, MN (US)

(73) Assignee: Boston Scientific Cardiac Diagnostics, Inc., Rochester, MN (US)

( * ) Notice: Subject to any disclaimer, the term of this patent is extended or adjusted under 35 U.S.C. 154(b) by 0 days.

(21) Appl. No.: 18/134,973

(22) Filed: Apr. 14, 2023

(65) Prior Publication Data

US 2023/0335244 A1    Oct. 19, 2023

Related U.S. Application Data

(60) Provisional application No. 63/332,051, filed on Apr. 18, 2022.

(51) Int. Cl.
*G16H 15/00* (2018.01)
*G16H 50/20* (2018.01)

(52) U.S. Cl.
CPC .............. *G16H 15/00* (2018.01); *G16H 50/20* (2018.01)

(58) Field of Classification Search
CPC ........ G16H 10/00; G16H 10/20; G16H 10/40; G16H 15/00; G16H 20/00; G16H 20/10;
(Continued)

(56) References Cited

U.S. PATENT DOCUMENTS

2013/0271470 A1* 10/2013 Moore .................. G16H 10/60
345/440.1
2013/0332487 A1* 12/2013 Ramesh ............. G06F 16/2455
707/775
(Continued)

OTHER PUBLICATIONS

Yuan et al. 2009, "A Metadata Registry to Facilitate the Search and Retrieval of Electrocardiograms," 2009 Ninth IEEE International Conference on Computer and Information Technology, Xiamen, China, 2009, pp. 269-273, doi: 10.1109/CIT.2009.106.*
(Continued)

*Primary Examiner* — Robert W Morgan
*Assistant Examiner* — Charles P Coleman
(74) *Attorney, Agent, or Firm* — Faegre Drinker Biddle & Reath LLP

(57) ABSTRACT

A method includes receiving, by a first computing system, a first package of electrocardiogram (ECG) data and metadata associated with the ECG data. The method further includes generating, by the first computing system, a report simulation page including strips of the ECG data and a summary of patient data based on the ECG data and the metadata. The method further includes displaying the report simulation page in a user interface (UI) and displaying a report build page in the UI. The report build page includes the ECG data and the metadata. The method further includes modifying the metadata in the report build page and automatically updating the report simulation page in response to the modifying the metadata.

20 Claims, 14 Drawing Sheets

(58) Field of Classification Search
CPC ........ G16H 20/13; G16H 20/17; G16H 30/00; G16H 40/00; G16H 50/00; G16H 70/00; G16H 80/00; G16H 50/20; G06Q 50/22–24
USPC .................................................. 705/2, 3, 20
See application file for complete search history.

(56) References Cited

U.S. PATENT DOCUMENTS

| | | | |
|---|---|---|---|
| 2015/0286782 A1* | 10/2015 | Ting | A61B 5/0816 600/509 |
| 2017/0315823 A1* | 11/2017 | Pennell | G06F 8/60 |
| 2019/0272920 A1 | 9/2019 | Teplitzky | |
| 2020/0160980 A1* | 5/2020 | Lyman | G06F 21/6254 |
| 2021/0118534 A1* | 4/2021 | Lyman | G06N 20/20 |
| 2021/0280283 A1* | 9/2021 | Finkelmeier | A61B 5/363 |
| 2021/0330270 A1 | 10/2021 | Ahmed et al. | |
| 2022/0095982 A1 | 3/2022 | De Saint Victor et al. | |
| 2022/0215918 A1* | 7/2022 | Yao | G06N 20/20 |
| 2022/0253510 A1* | 8/2022 | Montgomery | G06F 9/44526 |
| 2022/0336106 A1* | 10/2022 | Mcclanahan | G16H 50/70 |
| 2023/0355110 A1* | 11/2023 | Tran | G16H 40/20 |

OTHER PUBLICATIONS

Contreras et al. 2010, "System for acquisition and analysis of multichannel electrogastrogram," 2010 7th International Conference on Electrical Engineering Computing Science and Automatic Control, Tuxtla Gutierrez, Mexico, 2010, pp. 220-224, doi: 10.1109/ICEEE.2010.5608577.*

Heming et al. 2017, "The implementation of clinical data management and statistics system," 2017 29th Chinese Control And Decision Conference (CCDC), Chongqing, China, 2017, pp. 5299-5304, doi: 10.1109/CCDC.2017.7979439.*

International Search Report and Written Opinion received for PCT Patent Application No. PCT/US2023/018681, mailed on Jul. 20, 2023, 13 pages.

* cited by examiner

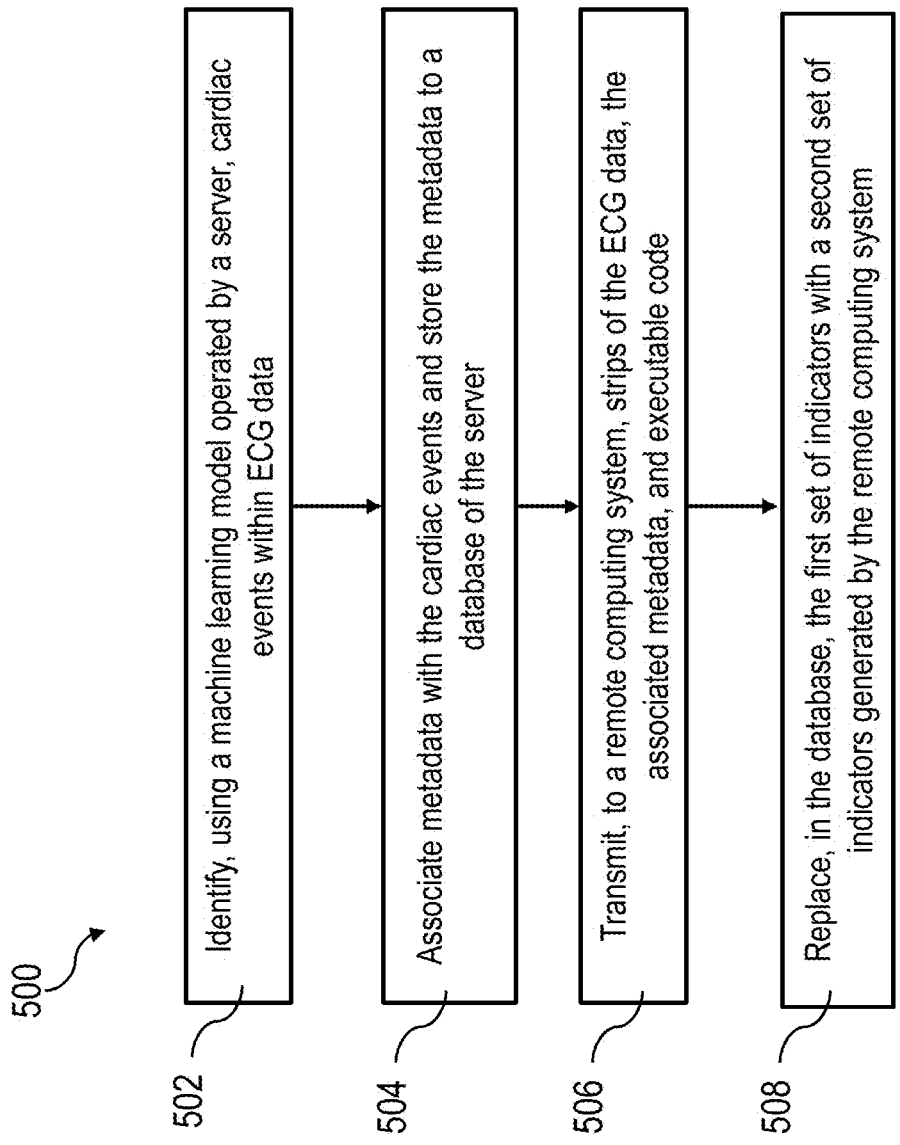

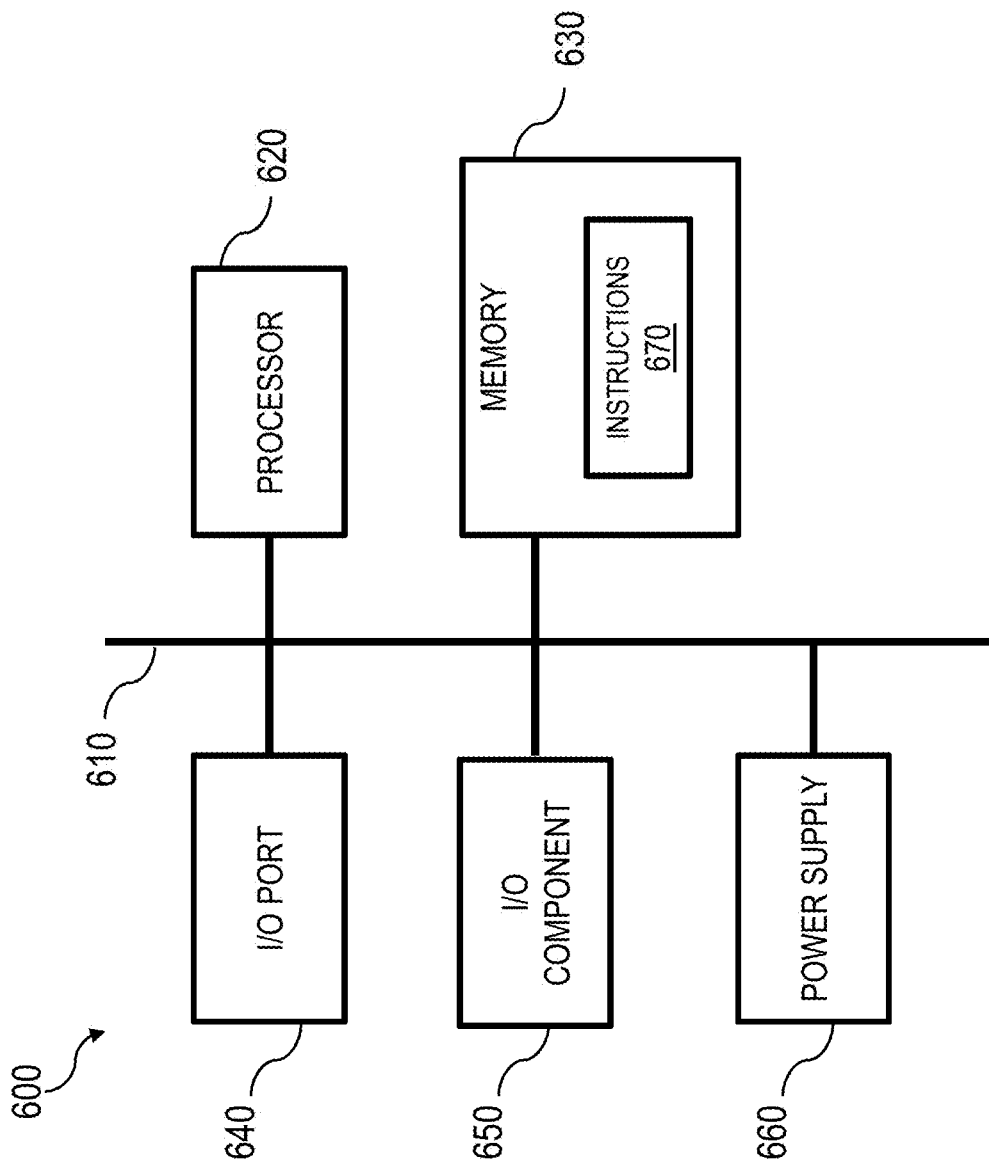

REAL-TIME ECG REPORT GENERATION

CROSS REFERENCE TO RELATED APPLICATION

This application claims priority to Provisional Application No. 63/332,051, filed Apr. 18, 2022, all of which are herein incorporated by reference in their entirety.

TECHNICAL FIELD

The present disclosure relates to devices, methods, and systems for analyzing cardiac activity and cardiac events.

BACKGROUND

Monitoring devices for collecting biometric data are becoming increasingly common in diagnosing and treating medical conditions in patients. For example, mobile devices can be used to monitor cardiac data in a patient. This cardiac monitoring can empower physicians with valuable information regarding the occurrence and regularity of a variety of heart conditions and irregularities in patients. Cardiac monitoring can be used, for example, to identify abnormal cardiac rhythms, so that critical alerts can be provided to patients, physicians, or other care providers and patients can be treated.

SUMMARY

In Example 1, a method includes receiving, by a first computing system, a first package of electrocardiogram (ECG) data and metadata associated with the ECG data. The method further includes generating, by the first computing system, a report simulation page including strips of the ECG data and a summary of patient data based on the ECG data and the metadata. The method further includes displaying the report simulation page in a user interface (UI) and displaying a report build page in the UI. The report build page includes the ECG data and the metadata. The method further includes modifying the metadata in the report build page and automatically updating the report simulation page in response to the modifying the metadata.

In Example 2, the method of Example 1, wherein the modifying includes changing a classification associated with a set of beats contained in the ECG data.

In Example 3, the method of Example 2, wherein the classification is a cardiac event type.

In Example 4, the method of any of the preceding Examples, wherein each beat contained in the ECG data is associated with a classification.

In Example 5, the method of any of the preceding Examples, wherein the automatically updating occurs at the first computing system.

In Example 6, the method of any of the preceding Examples, wherein the UI is displayed in a browser, wherein the automatically updating occurs without interaction with a server.

In Example 7, the method of any of the preceding Examples, wherein the first package of data further includes executable code, wherein the executable code is executed to cause the automatically updating the report simulation page.

In Example 8, the method of Example 7, wherein the executable code is executed to cause the displaying a report build page in the UI.

In Example 9, the method of any of the preceding Examples, wherein the report build page further includes a window displaying a set of beats of the ECG data that are associated with a first classification, wherein the modifying the metadata comprises changing the first classification to a second classification for each beat within the set of beats.

In Example 10, the method of any of the preceding Examples, wherein the metadata is generated by a machine learning model.

In Example 11, the method of any of the preceding Examples, further including: sending modified metadata to a server from the first computing system.

In Example 12, the method of any of the preceding Examples, further including: generating a report file containing the ECG data and the metadata displayed in the report simulation page.

In Example 13, a computer program product includes instructions to cause one or more processors to carry out the steps of the method of Examples 1-12.

In Example 14, a computer-readable medium having stored thereon the computer program product of Example 13.

In Example 15, a computer comprising the computer-readable medium of Example 14.

In Example 16, a system including a remote computing system with a user interface (UI), a first processor, and a first computer-readable medium having a first set of computer-executable instructions embodied thereon. The first set of instructions configured to be executed by the first processor to cause the first processor to: (1) generate a report simulation page including strips of the ECG data and a summary of patient data based on the ECG data and metadata associated with the ECG data, (2) display the report simulation page in the UI, (3) display a report build page in the UI, the report build page including the ECG data and the metadata, (4) modify the metadata in the report build page, and (5) automatically update the report simulation page in response to the modifying the metadata.

In Example 17, the system of Example 16, wherein the modifying includes changing a classification associated with a set of beats contained in the ECG data In Example 18, the system of Example 17, wherein the classification is a cardiac event type.

In Example 19, the system of Example 17, wherein the classification is a beat classification.

In Example 20, the system of Example 16, wherein the report build page further includes a window displaying a set of beats of the ECG data that are associated with a first beat classification, wherein the modifying the metadata comprises changing the first beat classification to a second beat classification for each beat in the set of beats.

In Example 21, the system of Example 16, wherein the automatically update occurs without interaction with a server.

In Example 22, the system of Example 16, further including a server with a database, a second processor, and a second computer-readable medium having a second set of computer-executable instructions embodied thereon. The second set of instructions configured to be executed by the second processor to cause the second processor to: (1) identify, using a machine learning model operated by the server, cardiac events within the ECG data, (2) associate the metadata with the ECG data, the metadata including a first set of indicators of cardiac event types, (3) store the metadata to the database of the server, and (4) transmit, to the remote computing system, strips of the ECG data and the associated metadata and first set of instructions.

In Example 23, the system of Example 22, wherein the second set of instructions are configured to be executed by the second processor to cause the second processor to: receive metadata comprising a second set of indicators of cardiac events generated by the remote computing system and replace the first set of indicators with the second set of indicators in the databases.

In Example 24, the system of Example 23, wherein the second set of instructions are configured to be executed by the second processor to cause the second processor to: generate a Holter report based, at least in part, on the ECG data and the second set of indicators.

In Example 25, the system of Example 23, wherein the second set of instructions are configured to be executed by the second processor to cause the second processor to: train the machine learning model using the second set of indicators.

In Example 26, a method including receiving, by a first computing system, a first package of electrocardiogram (ECG) data and metadata associated with the ECG data; generating, by the first computing system, a report simulation page including strips of the ECG data and a summary of patient data based on the ECG data and the metadata; displaying the report simulation page in a user interface (UI); displaying a report build page in the UI, the report build page including the ECG data and the metadata; modifying the metadata in the report build page; and automatically updating the report simulation page in response to the modifying the metadata.

In Example 27, the method of Example 26, wherein the modifying includes changing a classification associated with a set of beats contained in the ECG data.

In Example 28, the method of Example 27, wherein the classification is a cardiac event type.

In Example 29, the method of Example 27, wherein the classification is a beat classification.

In Example 30, the method of Example 26, wherein each beat contained in the ECG data is associated with a beat classification.

In Example 31, the method of Example 26, wherein the automatically updating occurs without interaction with a server.

In Example 32, a method includes receiving, by a server, electrocardiogram (ECG) data generated by a remote monitoring device; identifying, using a machine learning model operated by the server, cardiac events within the ECG data; associating metadata with the cardiac events and storing the metadata to a database of the server, the metadata comprising a first set of indicators of cardiac event types; transmitting, to a remote computing system, strips of the ECG data and the associated metadata and executable code; receiving, by the server from the remote computing system, metadata comprising a second set of indicators of cardiac events generated by the remote computing system; and replacing the first set of indicators with the second set of indicators in the database.

In Example 33, the method of Example 32, further comprising: generating a Holter report based, at least in part, on the ECG data and the second set of indicators.

In Example 34, the method of Example 32, wherein the executable code was used to generate the second set of indicators.

In Example 35, the method of claim 32, further comprising: training the machine learning model using the second set of indicators.

While multiple instances are disclosed, still other instances of the present disclosure will become apparent to those skilled in the art from the following detailed description, which shows and describes illustrative instances of the disclosure. Accordingly, the drawings and detailed description are to be regarded as illustrative in nature and not restrictive.

BRIEF DESCRIPTION OF THE DRAWINGS

FIG. 13 shows a flow diagram depicting an illustrative method for hosting a SaaS platform and updating a hosted database in response to changes to metadata made remotely, in accordance with instances of the disclosure.

FIG. 14 is a block diagram depicting an illustrative computing device, in accordance with instances of the disclosure.

Figure 1:
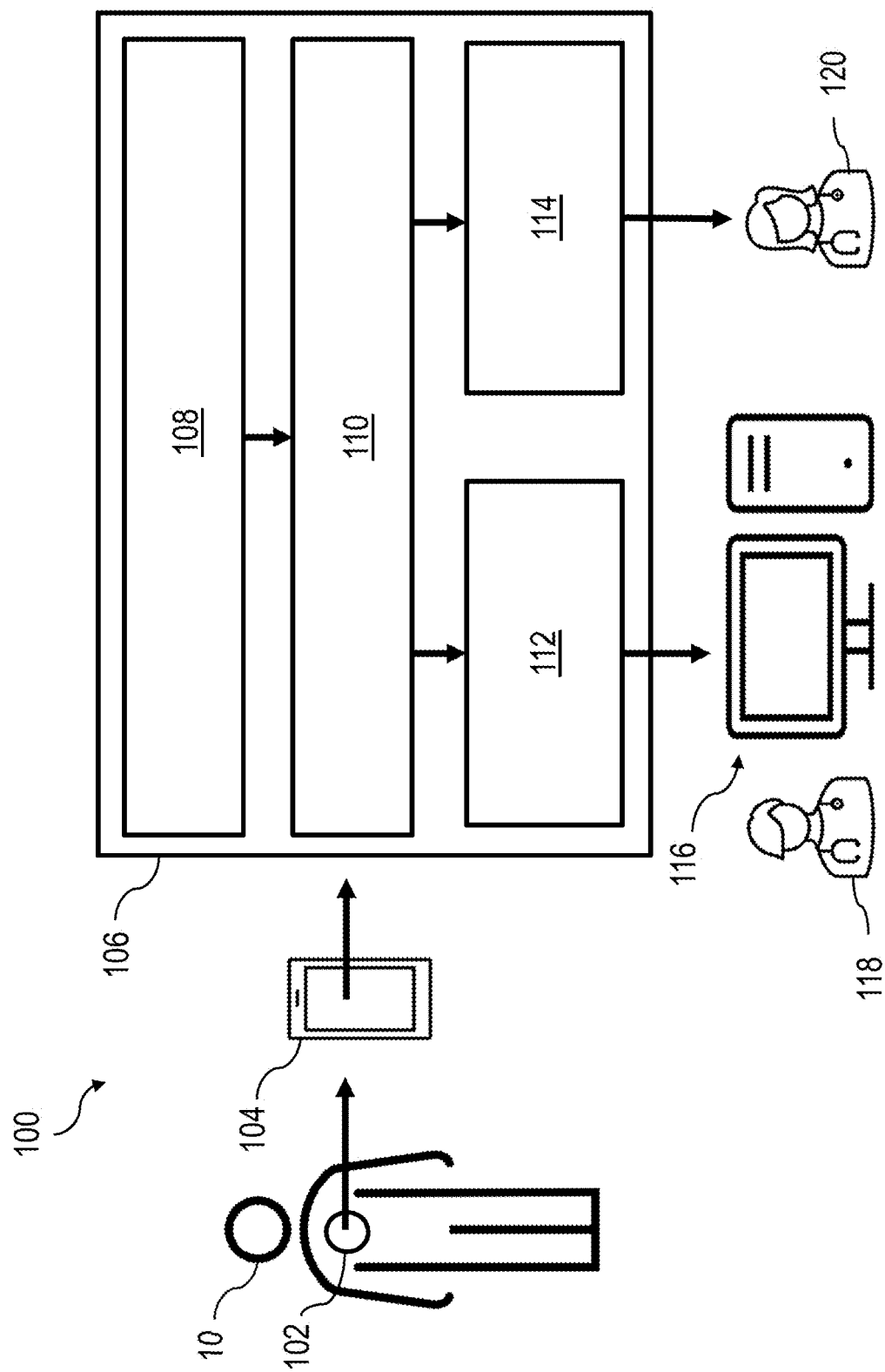
FIG. 1 shows a cardiac monitoring system, in accordance with certain instances of the present disclosure.

While the disclosed subject matter is amenable to various modifications and alternative forms, specific instances have been shown by way of example in the drawings and are described in detail below. The intention, however, is not to limit the disclosure to the particular instances described. On the contrary, the disclosure is intended to cover all modifications, equivalents, and alternatives falling within the scope of the disclosure as defined by the appended claims.

DETAILED DESCRIPTION

The present disclosure relates to devices, methods, and systems for facilitating analysis of cardiac activity and cardiac events (e.g., abnormal cardiac rhythms or other issues).

Electrocardiogram (ECG) data of a patient can be used to identify whether the patient has experienced a cardiac event. Because monitoring devices may be continuously sensing and recording ECG data, the amount of ECG data can be overwhelming and challenging to analyze efficiently. Instances of the present disclosure are accordingly directed to systems, methods, and devices for facilitating analysis of ECG data.

FIG. 1 illustrates a patient 10 and an example system 100. The system 100 includes a monitor 102 attached to the patient 10 to detect cardiac activity of the patient 10. The monitor 102 may produce electric signals that represent the cardiac activity in the patient 10. For example, the monitor 102 may detect the patient's heart beating (e.g., using infrared sensors, electrodes) and convert the detected heartbeat into electric signals representing ECG data. The monitor 102 communicates the ECG data to a mobile device 104 (e.g., a mobile phone).

The mobile device 104 may include a program (e.g., mobile phone application) that receives, processes, and analyzes the ECG data. For example, the program may analyze the ECG data and detect or flag cardiac events (e.g., periods of irregular cardiac activity) contained within the ECG data. As noted above, because ECG data may be getting continuously generated, the amount of ECG data can be overwhelming to store and process locally on the mobile device 104. As such, the mobile device 104 can periodically transmit chunks of the ECG data to another device or system, which can process, append together, and archive the chunks of the ECG data and metadata (e.g., time, duration, detected/flagged cardiac events) associated with the chunks of ECG data. In certain instances, the monitor 102 may be programmed to transmit the ECG data directly to the other device or system without utilizing the mobile device 104. Also, in certain instances, the monitor 102 and/or the mobile device 104 includes a button or touch-screen icon that allows the patient 10 to initiate an event. Such an indication can be recorded and communicated to the other device or system. In other instances involving multi-day studies, the ECG data and associated metadata are transmitted in larger chunks.

Cardiac Event Server

In the example shown in FIG. 1, the mobile device 104 transmits the ECG data (and associated metadata, if any) to a cardiac event server 106 (hereinafter "the server 106" for brevity). The server 106 includes multiple platforms, layers, or modules that work together to process and analyze the ECG data such that cardiac events can be detected, filtered, prioritized, and ultimately reported to a patient's physician for analysis and treatment. In the example of FIG. 1, the server 106 includes one or more machine learning models 108 (e.g., types of deep neural networks), a cardiac event router 110, a report platform 112, and a notification platform 114. Although only one server 106 is shown in FIG. 1, the server 106 can include multiple separate physical servers, and the various platforms/modules/layers can be distributed among the multiple servers. Each of the platforms/modules/layers can represent separate programs, applications, and/or blocks of code where the output of one of the platforms/modules/layers is an input to another of the platforms/modules/layers. Each platform/module/layer can use application programming interfaces to communicate between or among the other platforms/modules/layers as well as systems and devices external to the server 106.

The server 106 applies the machine learning model 108 to the ECG data to classify cardiac activity of the patient 10. For example, the machine learning model 108 may compare the ECG data to labeled ECG data to determine which labeled ECG data the ECG data most closely resembles. The labeled ECG data may identify a particular cardiac event, including but not limited to ventricular tachycardia, bradycardia, atrial fibrillation, pause, normal sinus rhythm, or artifact/noise.

In certain embodiments, the machine learning model 108 includes two paths, where the first path is a deep convolutional neural network and the second path is a deep fully-connected neural network. The deep convolutional neural network receives one or more sets of beats (e.g., beat trains with 3-10 beats) which are processes through a series of layers in the deep convolutional neural network. The series of layers can include a convolution layer to perform convolution on time series data in the beat trains, a batch normalization layer to normalize the output from the convolution layer (e.g., centering the results around an origin), and a non-linear activation function layer to receive the normalized values from the batch normalization layer. The beat trains then pass through a repeating set of layers such as another convolution layer, a batch normalization layer, a non-linear activation function layer. This set of layers can be repeated multiple times.

The deep fully connected neural network receives RR-interval data (e.g., time intervals between adjacent beats) and processes the RR-interval data through a series of layers: a fully connected layer, a non-linear activation function layer, another fully connected layer, another non-linear activation function layer, and a regularization layer. The output from the two paths is then provided to the fully connected layer. The resulting values are passed through a fully connected layer and a softmax layer to produce probability distributions for the classes of beats.

If the machine learning model 108 determines that the ECG data most closely resembles a labeled ECG data associated with a cardiac event, then the machine learning model 108 may determine that the patient 10 has experienced that cardiac event. Additionally, the machine learning model 108 may measure or determine certain characteristics of the cardiac activity of the patient 10 based on the ECG data. For example, the machine learning model 108 may determine a heart rate, a duration, or a beat count of the patient 10 during the cardiac event based on the ECG data. The server 106 stores the cardiac event (and associated metadata such as information like heart rate, duration, beat count, etc.) in a database for storage. Subsequently, the server 106 may retrieve the cardiac event and associated information from the database.

In certain instances, the mobile device 104 (or monitor 102) may initially classify a cardiac event based on the ECG data. The server 106 may then re-classify or confirm the cardiac event using the machine learning model 108. Doing so allows for a more computationally-expensive analysis of the ECG data to be performed using the computing resources of the server 106, rather than the limited resources of the mobile device 104.

In certain instances, once the ECG data is processed by the machine learning model 108, the ECG data is made available for the report platform 112. As will be described in more detail below, the report platform 112 can be accessed by a remote computer 116 (e.g., client device such as a laptop, mobile phone, desktop computer, and the like) by a user at a clinic or lab 118.

In other instances, the cardiac event router 110 is used to determine what platform further processes the ECG data based on the classification associated with the cardiac event. For example, if the identified cardiac event is severe, the cardiac event router 110 can flag or send the ECG data, etc., to the notification platform 114. The notification platform 114 can be programmed to send notifications (along with relevant ECG data and associated metadata) immediately to the patient's physician/care group remote computer 116 and/or to the patient 10 (e.g., to their computer system, e-mail, mobile phone application).

Report Platform

Figure 2:
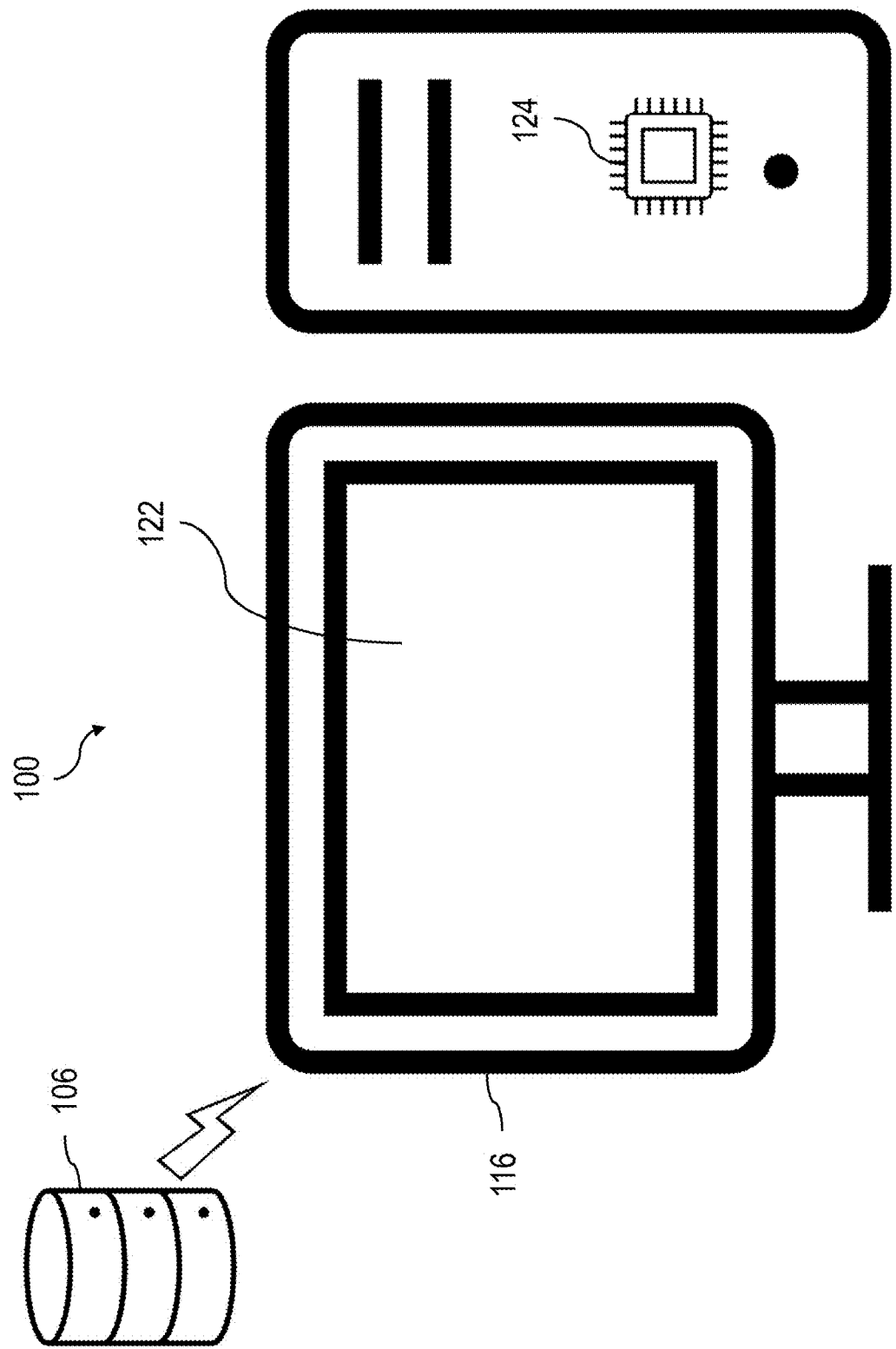
FIG. 2 shows a server, remote computer, and user interface, in accordance with certain instances of the present disclosure.

FIG. 2 shows the server 106 communicatively coupled (e.g., via a network) to the remote computer 116. In the example of FIG. 2, the remote computer 116 includes a monitor showing a user interface 122 (hereinafter "the UI 122" for brevity) that displays features of the report platform 112 hosted by the server 106. The UI 122 includes multiple pages or screens for tracking and facilitating analysis of patient ECG data.

Figure 3:
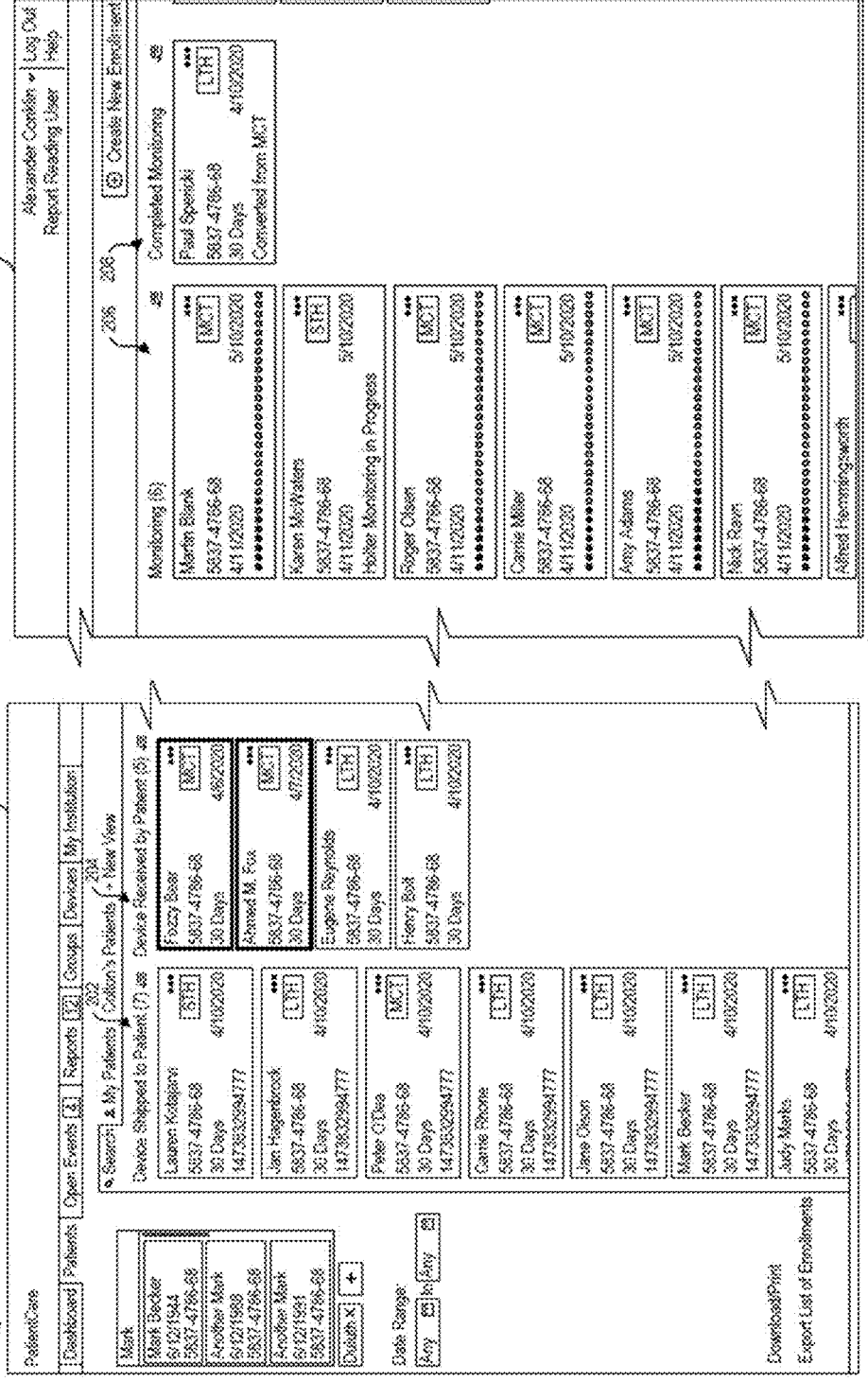
FIG. 3 shows the user interface of FIG. 2, in accordance with certain instances of the present disclosure.

FIG. 3 shows a closer-up view of the UI 122 and a patient dashboard page 200. The patient dashboard page 200 displays a summary of statuses of patients being monitored. For example, the patient dashboard page 200 can display a list 202 of patients who have been shipped a monitoring device, a list 204 of patients who have received a monitoring device, a list 206 of patients currently being monitored (e.g., a monitor is actively recording ECG data), and a list 208 of patients who have completed the monitoring period.

Figure 4:
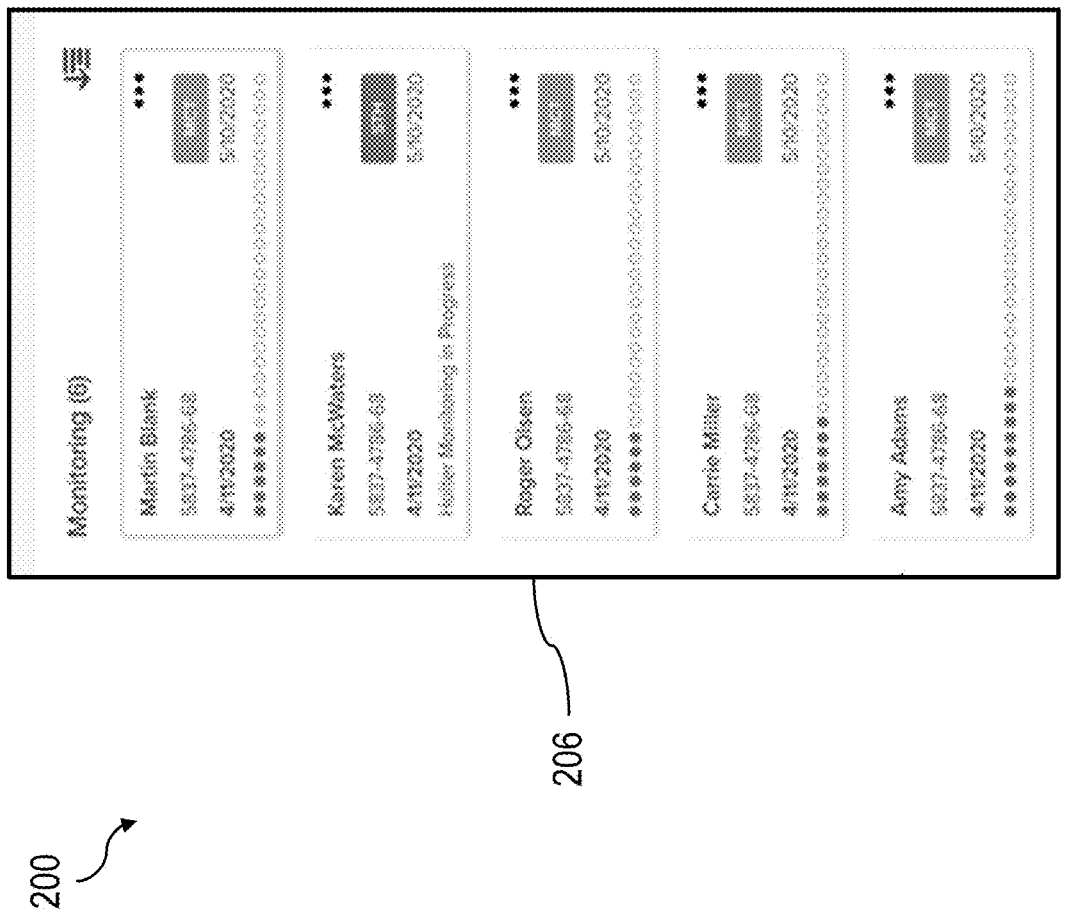
FIGS. 4-8B show various views of a report building user interface, in accordance with certain instances of the present disclosure.

FIG. 4 shows a closer-up view of the list 206 of patients currently being monitored. The list 206 can show information about each patient, including the current status of their monitoring. For example, the list 206 can include a set of icons that are colored to indicate the progress and completeness of the monitoring period. For example, the icons can be colored green for each day (or other time period) the patient has successfully collected a sufficient amount of ECG data, colored yellow for time periods where the monitored ECG data is intermittent (e.g., time periods where the patient removed the monitor at certain periods), colored red for time periods with insufficient ECG data, and blank for time periods the patient has yet to complete. As such, the patient dashboard page 200 can facilitate tracking of patient monitoring and when studies are complete and ready to build and generate reports.

Build and Report Screens

In certain instances, the report platform 112 is a software-as-a-service (SaaS) platform hosted by the server 106. To access the report platform 112, a user (e.g., a technician) interacts with the UI 122 to log into the report platform 112 via a web browser such that the user can use and interact with the report platform 112. When the user at the clinic or lab 118 is ready to analyze ECG data of a patient, the user can select a patient's profile through the UI 122.

The server 106 (e.g., via programming associated with the report platform 112) can start a process for sending data to the remote computer 116. This data includes the ECG data and metadata associated with the ECG data. As noted above, once the ECG data from the monitored patients has been collected, the machine learning model 108 may determine certain characteristics of the cardiac activity of the patient 10 based on the ECG data, including estimating that a cardiac event has occurred and associating or generating metadata for the determined events. The metadata can include information about the patient 10, a heart rate of the patient 10 during the cardiac event, a duration of the cardiac event, a beat count of the cardiac event, a confidence level of the machine learning model's identification of the cardiac event, and/or a beat classification (e.g., normal, ventricular, supraventricular, unclassified). As described in more detail below, in certain embodiments, the machine learning model 108 assigns each beat with a beat classification and also assigns, for certain groups and patterns of beats, a cardiac event type (e.g., atrial fibrillation, ventricular tachycardia, flutter). To distinguish among the beats, each individual beat can therefore be assigned a unique identifier (e.g., a unique number).

Accessing, processing, and displaying one or more days' worth of ECG data and metadata can consume a large amount of computing resources, network bandwidth resources, and human resources. To help alleviate burdens on these resources, the server 106 (e.g., via the report platform 112) can selectively transmit packages of ECG data and metadata to the remote computer 116.

The initial packages of data can include: (1) short strips (e.g., 60-second strips) of ECG data surrounding detected cardiac events, (2) metadata associated with the strips, and (3) executable code (e.g., JavaScript code). In certain instances, only the ECG data associated with highest priority cardiac events are initially transferred. After the initial packages of data are transmitted from the server to the remote computer 116, additional packages of data can be transmitted in response to selections made by the user in the UI 122.

Figure 7:
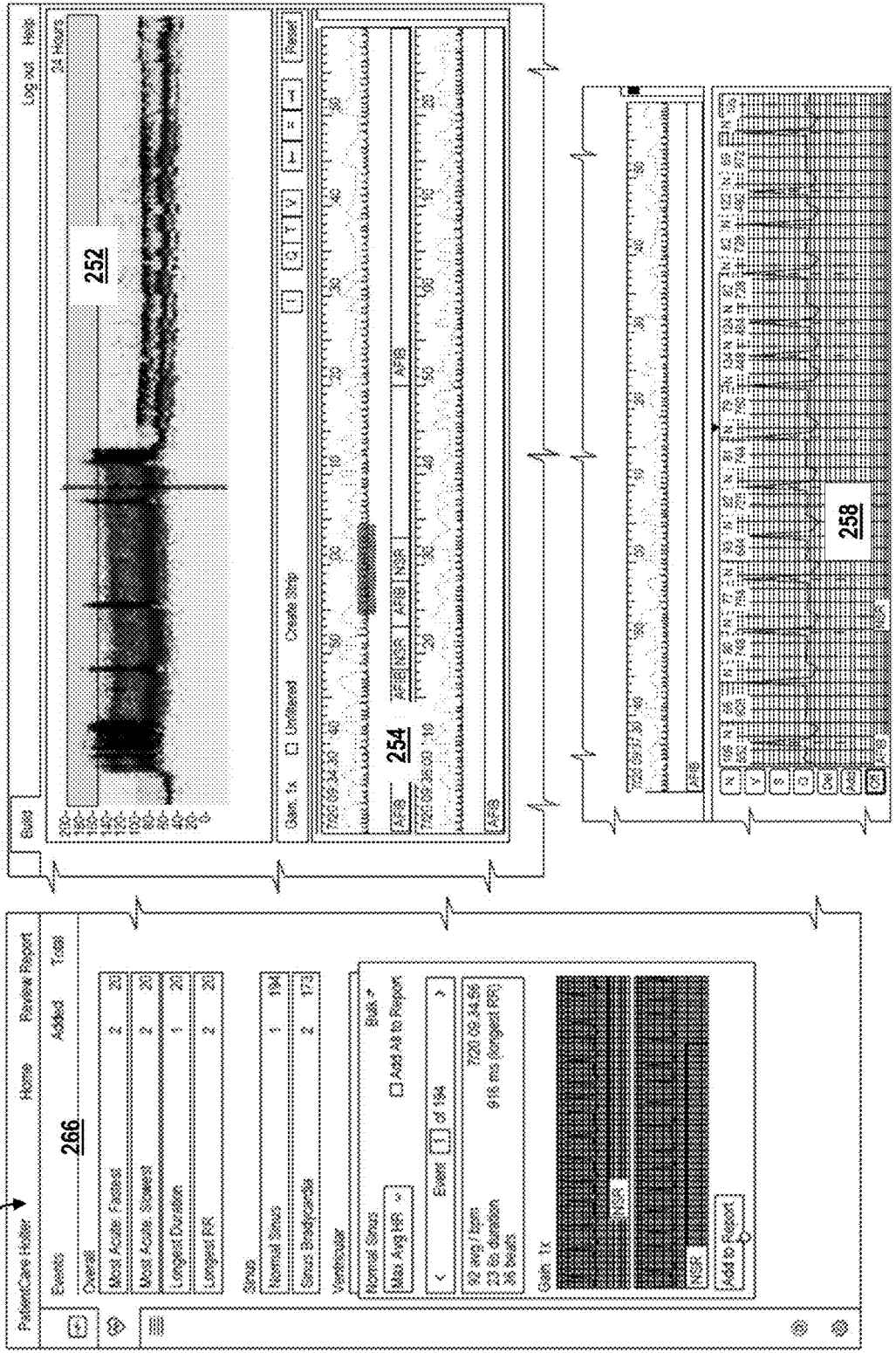
Figure 8B:
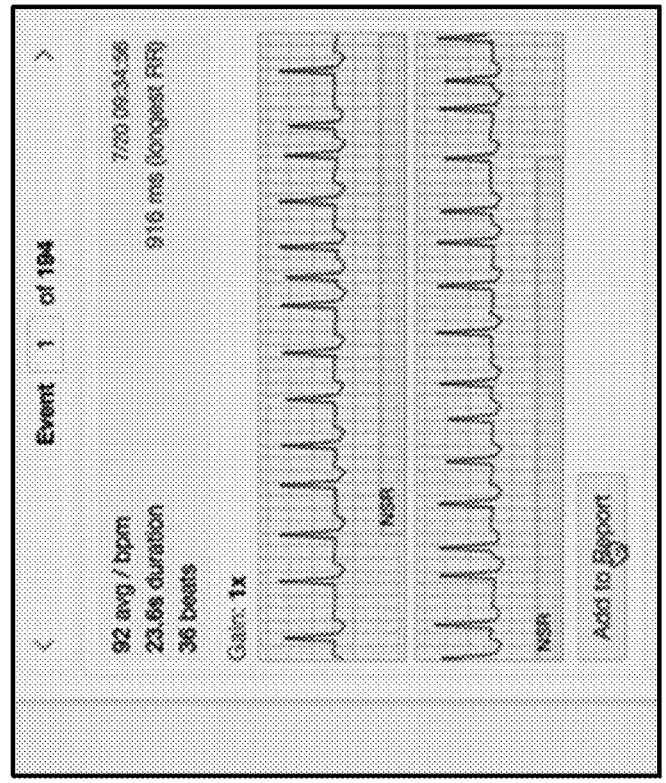
Figure 8A:
Figure 9:
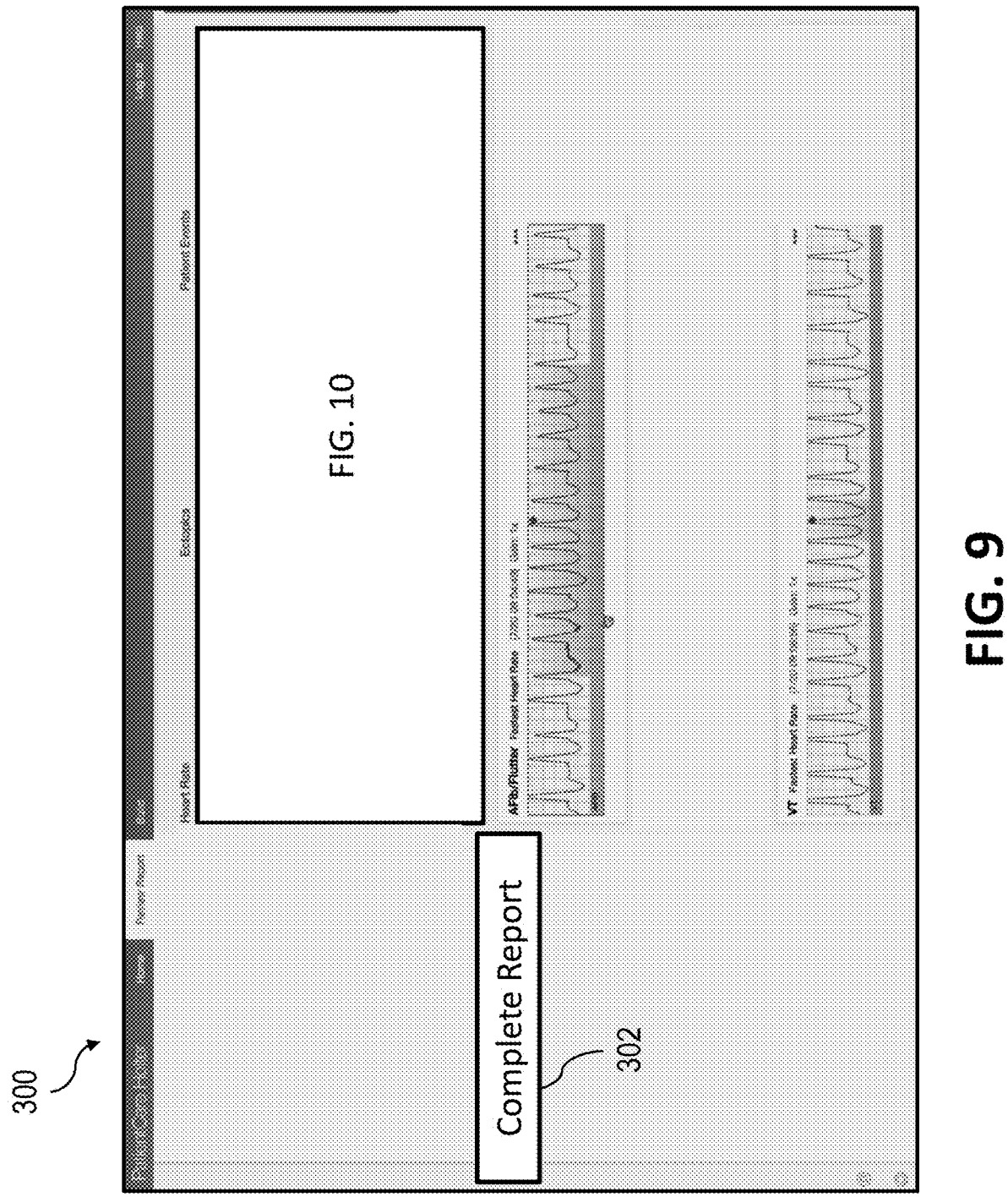
FIGS. 9-11 show various views of a report building user interface, in accordance with certain instances of the present disclosure.
Figure 10:
Figure 11:
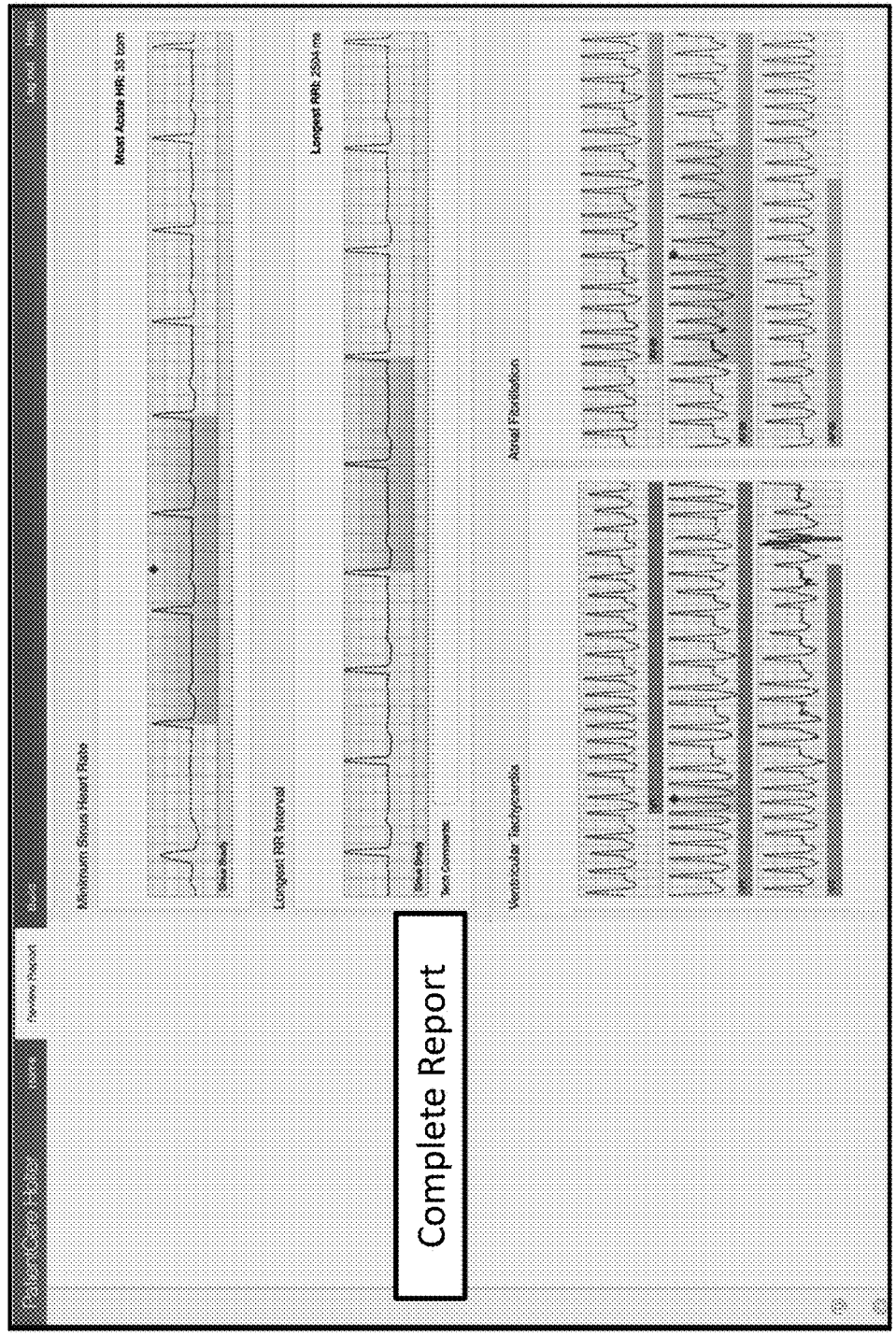

With these initial packages of data, the user has access (via the remote computer 116 and the UI 122) to a report build page 250 shown in FIGS. 5-8B and a report simulation page 300 shown in FIGS. 9-11. The report build page 250 facilitates analysis of cardiac events, and the report simulation page 300 facilitates review of a summary of the various cardiac events and a patient's ECG data and metadata. These pages are generated at the remote computer 116 based on the packages of data and they are selectively displayed via the UI 122. As will be described in more detail below, as the user interacts with the report build page 250, the report simulation page 300 is updated in real time. This real-time updating allows the user to quickly preview the ECG data and metadata set for inclusion in a final report without needing to wait for a final report to be generated. Although the report build page 250 and the report simulation page 300 are shown in separate Figures, the UI 122 could simultaneously display both of these pages so that the user can view updates to the report simulation page 300 as they occur without needing to switch between the two pages. Put another way, aspects of FIGS. 5-8B and aspects of FIGS. 9-11 could be simultaneously displayed in the UI 122 so that the user can view both pages.

Figure 5:
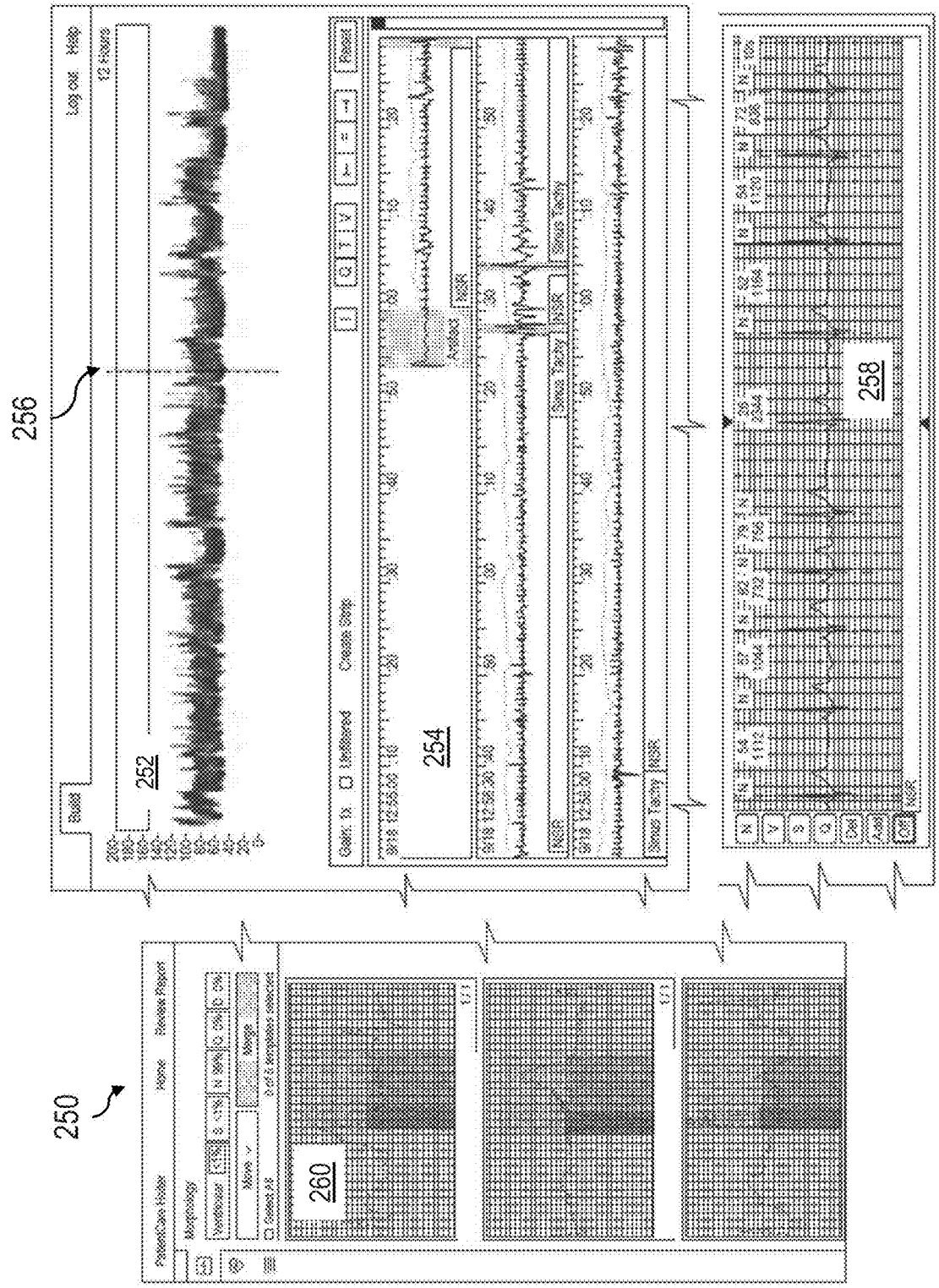

FIG. 5 shows a screenshot of the report build page 250. The report build page 250 is used by a user to review and analyze a patient's ECG data and metadata. The report build page 250 includes multiple windows for displaying data, plots, icons, links, markers, indicators, and the like.

Window 252 displays a heart rate plot of multiple days' worth of ECG data. This window 252 provides an initial visual insight into which periods of time appear to contain abnormal heart rate activity. In the example of FIG. 5, the window 252 displays four days of ECG data, although shorter or longer time periods could be displayed by default or changed by the user.

Window 254 allows the user to view a shorter plot of ECG data. For example, the window 254 may display ECG data associated with a detected cardiac event along with ECG data preceding and following the detected event. This window 254 provides visual insight into the onset of a detected event and whether the detected event is perhaps an artifact, follow-on event, etc. As the user scrolls through the window 254, the window 252 displays an indicator 256 (e.g., a vertical line) showing the location of the ECG data of window 254 within the heart rate plot of window 252.

Window 258 shows a plot of ECG data (e.g., approximately 10 beats) that is shorter than the plots of windows 252 and 254. Window 258 displays a closer-up view of a portion of the ECG data of windows 252 and 254. The user can use window 254 to select which shorter set of ECG data is displayed in the window 258. Each of the windows 252, 254, and 258 can include markers, indicators, icons, etc., to visually note the location of detected cardiac events within the strips of ECG data.

To the left of the report build page 250 is a beat morphology window 260 (hereinafter "the morphology window 260"), which includes multiple individual sub-windows that display plots of one or more individual beats. The user can use the morphology window 260 to select beats, which can result in updating the windows 252, 254, and 258. For example, the indicator 256 in window 252 can move to location of the selected beat and/or the beat can be highlighted within the plot, and the windows 252, 254, and 258 can be updated to show ECG data surrounding the beat selected in the morphology window 260.

Figures 6A, 6B:
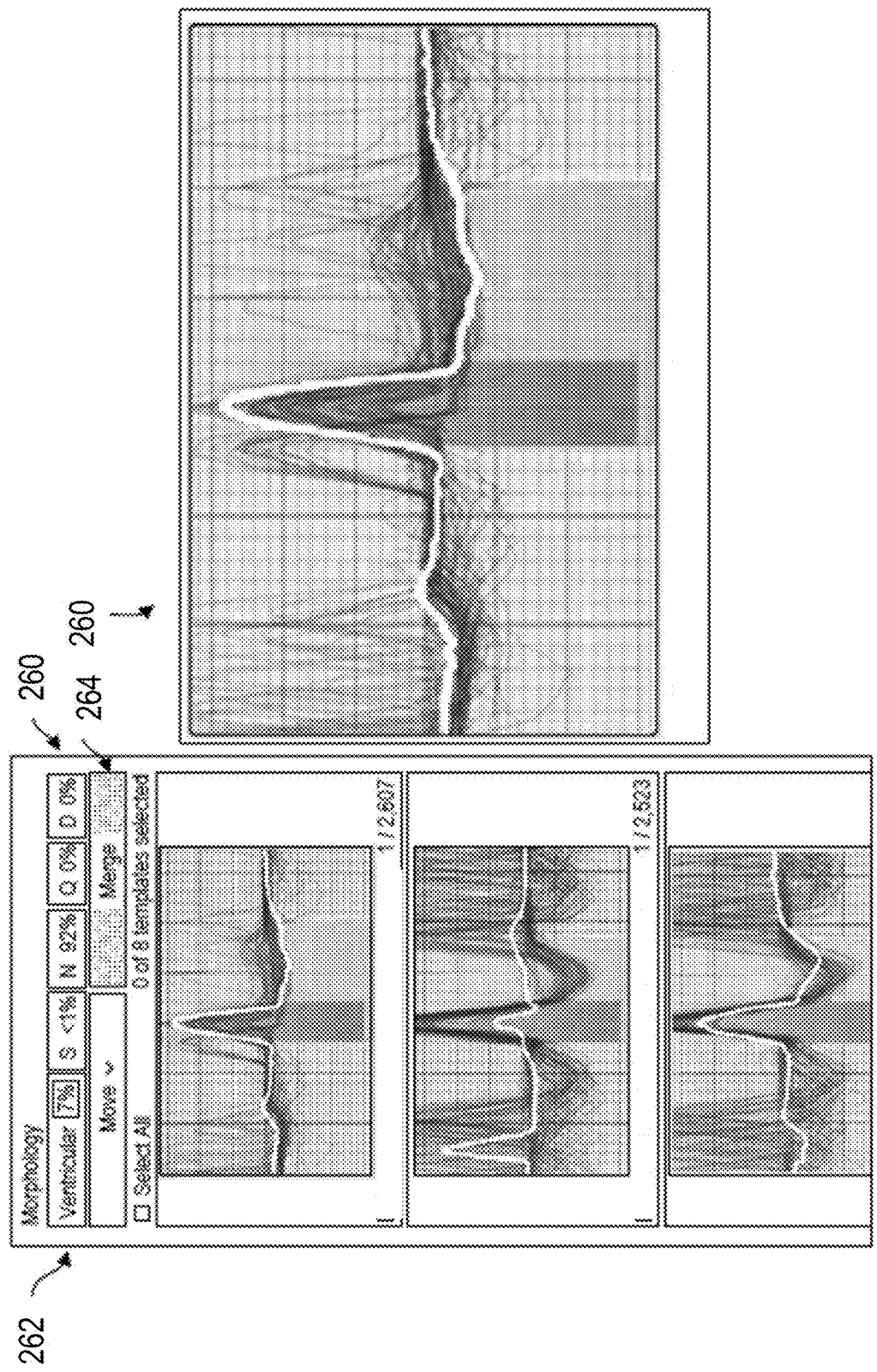

FIGS. 6A and 6B show closer-up views of the morphology window 260. FIG. 6A shows the morphology window 260 as displaying multiple sub-windows. Each sub-window can display multiple plots of beats that have been characterized (e.g., by the machine learning model 108) with the same type of cardiac event. The user can select the type of cardiac event (e.g., atrial fibrillation, ventricular tachycardia) from a menu button 262 to display beats associated with the selected cardiac event in the sub-window.

The user can then select individual or sets of beat plots in the sub-window and, if desired, change the type of cardiac event the selected beats are associated with or the beat classification. Additionally, instead of selecting individual beats, the user can select all beats associated with a given cardiac event and change that given cardiac event (or beat classification) to a different type of cardiac event (or beat classification). Because the machine learning model 108 assigns each beat with an initial beat classification, the report build page 250 can be used to make mass updates to the metadata associated with similarly characterized beats. For example, in FIG. 6B, the cardiac event type associated with the sub-window is shown as being associated with 2,607 beats. Using the morphology window 260 of the report build page 250, the user can recharacterize each of those 2,607 beats with one operation. As such, metadata for thousands to hundreds of thousands (or millions, for long studies) of beats can be updated en masse. The user can also merge sub-windows using a merge button 264 such that the beats in the two or more sub-windows are characterized with the same cardiac event type.

Because a set of ECG data may represent tens of thousands, hundreds of thousands, or even millions of individual beats, this ability to make mass updates to beats saves the user time in analyzing ECG data and, ultimately, building a report.

FIG. 7 shows another screenshot of the report build page 250, which is displaying an event window 266. FIGS. 8A and 8B show closer-up views of the event window 266. As shown in FIG. 8A, the event window 266 includes a list of events for analysis. The initial list of events (and initial candidates of detected events and associated ECG data) can be automatically generated and populated by the report platform 112. The user can use the initial list of events as a "to-do" list of analysis that should be performed and added to a final report. For example, each report can include the fastest beat(s), the slowest beat(s), the longest duration, the longest RR, and examples of cardiac events experienced by the patient. As the user runs through the list of events, the event window 266 can display the strips of ECG data (as shown in FIG. 8B) associated with the detected events identified as being top candidates for inclusion in the report. Further, as the user runs through the list of events, the rest of the windows 252, 254, and 258 (shown in FIG. 7) are updated to show ECG data surrounding the detected event. In certain instances, when the user is analyzing a particular type of cardiac event, the window 252 will show ECG data associated with the particular type of cardiac event in a different color or other visual distinction from the rest of the ECG data.

FIGS. 9-11 show different screenshots of the report simulation page 300. The initial ECG data, metadata, and strips of ECG data shown in the report simulation page 300 can be generated by the report platform 112. That is, when the user initially selects the report simulation page 300, the user is viewing an initial simulated report that was automatically generated by the report platform 112. The simulated report mimics the formatting and data that would ultimately be included in a finalized report sent to the patient's physician. Example finalized reports include Holter reports (e.g., short-term or long-term) and cardiac event reports, and the reports can be in the form of a pdf file or other file type.

Because the simulated report displayed on the report simulation page 300 mimics the final report, the simulated report allows the user to see a preview of the final report without needing to spend the time generating an actual finalized report, which can take 10-20 minutes. Thus, the report simulation page 300 saves the user time from having to create multiple reports before settling on a final version that is then sent to the patient's physician.

The report simulation page 300 includes a baseline summary of patient information generated from the ECG data. For example, as shown in FIG. 10, the report simulation page 300 includes a summary of heart rate information, ectopics, and events—each of which may have been initially been generated by the machine learning model 108. For a given type of event, as shown in FIGS. 9 and 11, the report simulation page 300 includes one or more example strips of ECG data.

The report simulation page 300 can be automatically updated in real-time as the user makes changes in the report build page 250. For example, if the user uses the morphology window 260 of the report build page 250 to recharacterize beats with a different type of cardiac event, the report simulation page 300 will be updated to reflect the change. This updating of data may include automatically changing the order of cardiac events on the report simulation page 300, changing which strip of ECG data is representative of a given cardiac event, and/or updating the baseline summary of patient information generated from the ECG data, among other things. Further, as the user selects representative events on the report build page 250, those events are automatically added to the report simulation page 300.

To save processing and network resources and to allow these changes to occur in real-time, the calculations and changes to the report simulation page 300 can be carried out locally on the remote computer 116—as opposed to sending large chunks of data back and forth between the server 106 and the remote computer 116. For example, the calculations can be carried out using cache memory 124 (shown in FIG. 1) and processing capabilities (e.g., one or more microprocessors) of the remote computer 116. To enable local processing and updating, the report platform 112 can send the remote computer 116 code to execute locally. This code uses (or operates on) the outputs of the machine learning model 108 such as the beat classifications and rhythm classifications (as opposed to the underlying or raw ECG data), which reduces the computational resources needed to process the changes made by user locally at the remote computer 116. In certain embodiments, this code is executed by an internet browser operating on the remote computer 116.

Once the user is satisfied with the simulated report, the user can select the "Complete Report" button on the report simulation page 300. This selection will start the process of generating a final report to be sent to the patient's physician.

In certain instances, once the report is built and complete, the remote computer 116 can send any changes to the metadata (e.g., the beat classifications and the rhythm classifications) to the server 106 and its database. The server 106 can then replace the metadata initially created by the machine learning model (and saved to the database) with the metadata generated by the remote computer while the user was reviewing and editing the metadata. As such, if the ECG and metadata need to be accessed again, the server's database has the most recent version of the metadata. Further, machine learning model may be further trained on the metadata generated by the user at the remote computer.

Methods

Figure 12:
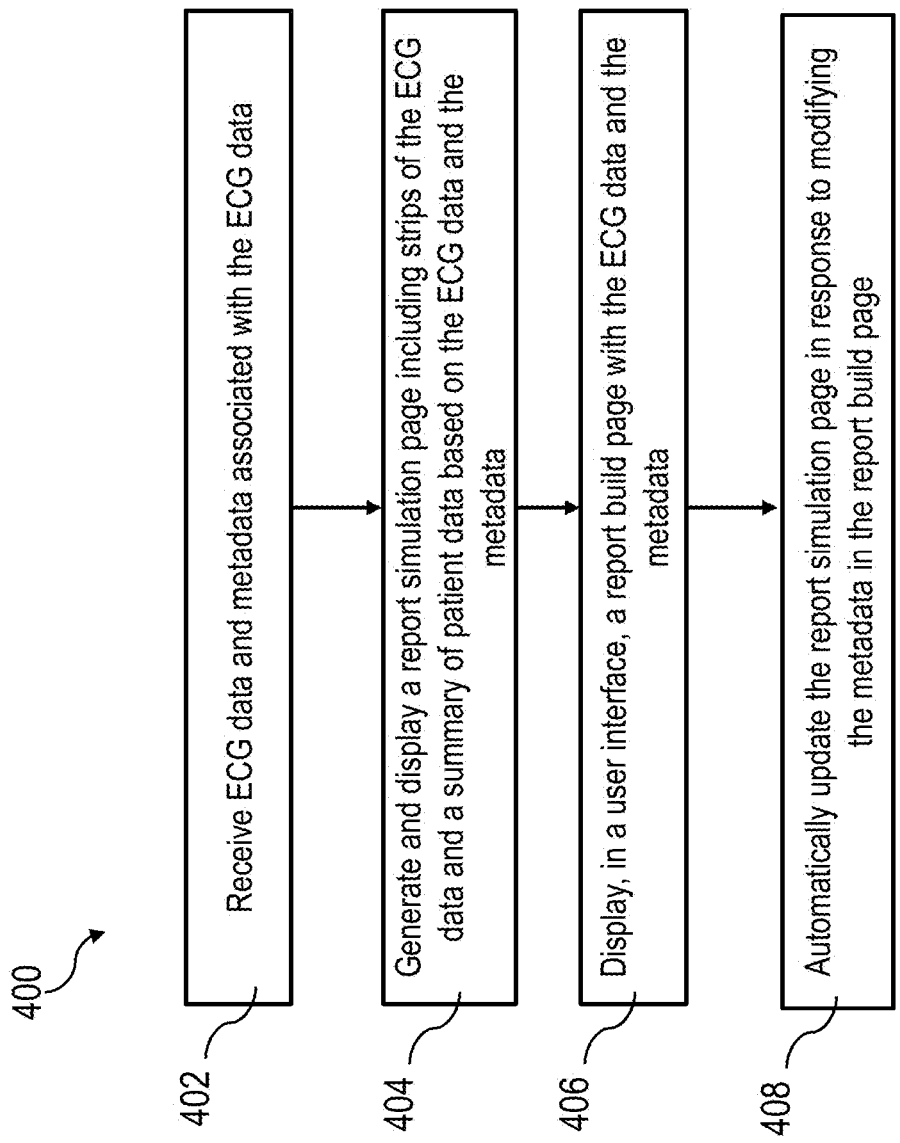
FIG. 12 shows a flow diagram depicting an illustrative method for real-time displaying of ECG data and updating metadata, in accordance with instances of the disclosure.

FIG. 12 shows a block diagram of a method 400 for real-time displaying of ECG data and updating metadata. The method 400 includes receiving, by a first computing system, a first package of electrocardiogram (ECG) data and metadata associated with the ECG data (block 402 in FIG. 12). The method 400 further includes generating and displaying, by the first computing system, a report simulation page including strips of the ECG data and a summary of patient data based on the ECG data and the metadata (block 404 in FIG. 12). The method 400 further includes displaying, in a user interface, a report build page with the ECG data and the metadata (block 406 in FIG. 12). The method 400 further includes automatically updating the report simulation page in response to modifying the metadata in the report build page (block 408 in FIG. 12).

FIG. 13 shows a block diagram of a method 500 for hosting a SaaS platform and updating a hosted database in response to changes to metadata made remotely. The method 500 includes identifying, using a machine learning model operated by a server, cardiac events within the ECG data (block 502 in FIG. 13). The method 500 further includes associating metadata with the cardiac events and storing the metadata to a database of the server (block 504 in FIG. 13). The metadata comprises a first set of indicators of cardiac event types. Next, the method 500 includes transmitting, to a remote computing system, strips of the ECG data and the associated metadata and executable code (block 506 in FIG. 13). The method further includes replacing, in the database, the first set of indicators with a second set of indicators generated by the remote computing system (block 508 in FIG. 13).

Computing Devices and Systems

FIG. 14 is a block diagram depicting an illustrative computing device 600, in accordance with instances of the disclosure. The computing device 600 may include any type of computing device suitable for implementing aspects of instances of the disclosed subject matter. Examples of computing devices include specialized computing devices or general-purpose computing devices such as workstations, servers, laptops, desktops, tablet computers, hand-held devices, smartphones, general-purpose graphics processing units (GPGPUs), and the like. Each of the various components shown and described in the Figures can contain their own dedicated set of computing device components shown in FIG. 14 and described below. For example, the mobile device 104, the server 106, and the remote computer 116 can each include their own set of components shown in FIG. 14 and described below.

In instances, the computing device 600 includes a bus 610 that, directly and/or indirectly, couples one or more of the following devices: a processor 620, a memory 630, an input/output (I/O) port 640, an I/O component 650, and a power supply 660. Any number of additional components, different components, and/or combinations of components may also be included in the computing device 600.

The bus 610 represents what may be one or more busses (such as, for example, an address bus, data bus, or combination thereof). Similarly, in instances, the computing device 600 may include a number of processors 620, a number of memory components 630, a number of I/O ports 640, a number of I/O components 650, and/or a number of power supplies 660. Additionally, any number of these components, or combinations thereof, may be distributed and/or duplicated across a number of computing devices.

In instances, the memory 630 includes computer-readable media in the form of volatile and/or nonvolatile memory and may be removable, nonremovable, or a combination thereof. Media examples include random access memory (RAM); read only memory (ROM); electronically erasable programmable read only memory (EEPROM); flash memory; optical or holographic media; magnetic cassettes, magnetic tape, magnetic disk storage or other magnetic storage devices; data transmissions; and/or any other medium that can be used to store information and can be accessed by a computing device. In instances, the memory 630 stores computer-executable instructions 670 for causing the processor 620 to implement aspects of instances of components discussed herein and/or to perform aspects of instances of methods and procedures discussed herein. The memory 630 can comprise a non-transitory computer readable medium storin the computer-executable instructions 670.

The computer-executable instructions 670 may include, for example, computer code, machine-useable instructions, and the like such as, for example, program components capable of being executed by one or more processors 620 (e.g., microprocessors) associated with the computing device 600. Program components may be programmed using any number of different programming environments, including various languages, development kits, frameworks, and/or the like. Some or all of the functionality contemplated herein may also, or alternatively, be implemented in hardware and/or firmware.

According to instances, for example, the instructions 670 may be configured to be executed by the processor 620 and, upon execution, to cause the processor 620 to perform certain processes. In certain instances, the processor 620, memory 630, and instructions 670 are part of a controller such as an application specific integrated circuit (ASIC), field-programmable gate array (FPGA), and/or the like. Such devices can be used to carry out the functions and steps described herein.

The I/O component 650 may include a presentation component configured to present information to a user such as, for example, a display device, a speaker, a printing device, and/or the like, and/or an input component such as, for example, a microphone, a joystick, a satellite dish, a scanner, a printer, a wireless device, a keyboard, a pen, a voice input device, a touch input device, a touch-screen device, an interactive display device, a mouse, and/or the like.

The devices and systems described herein can be communicatively coupled via a network, which may include a local area network (LAN), a wide area network (WAN), a cellular data network, via the internet using an internet service provider, and the like.

Aspects of the present disclosure are described with reference to flowchart illustrations and/or block diagrams of methods, devices, systems and computer program products. It will be understood that each block of the flowchart illustrations and/or block diagrams, and combinations of blocks in the flowchart illustrations and/or block diagrams, can be implemented by computer program instructions.

Various modifications and additions can be made to the exemplary instances discussed without departing from the scope of the disclosed subject matter. For example, while the instances described above refer to particular features, the scope of this disclosure also includes instances having different combinations of features and instances that do not include all of the described features. Accordingly, the scope of the disclosed subject matter is intended to embrace all such alternatives, modifications, and variations as fall within the scope of the claims, together with all equivalents thereof.

We claim:

1. A system comprising:
a remote computing system comprising a user interface (UI) and one or microprocessors,
wherein the remote computing system is configured to receive executable code, packages of electrocardiogram (ECG) data, and associated metadata from a server,
wherein the executable code is configured to be executed by the one or more mocroprocessors locally on the remote computing system to:
generate a report simulation page including strips of the ECG data and a summary of patient data based on the ECG data and the metadata associated with the ECG data,
display the report simulation page in the UI,
display a report build page in the UI, the report build page including the ECG data and the metadata,
modify the metadata in the report build page by changing a classification associated with a set of beats contained in the ECG data,
calculate, using the executable code operated at the remote computing system, updated metadata as a result of the classification being changed, and
automatically update the report simulation page in response to the updated metadata.

2. The system of claim 1, wherein the classification is a cardiac event type, wherein the updated metadata is an updated set of beat classifications.

3. The system of claim 1, wherein the classification is a beat classification, wherein the updated metadata is an updated set of cardiac event classifications.

4. The system of claim 1, wherein the report build page further includes a window displaying a set of beats of the ECG data that are associated with a first beat classification, wherein the modifying the metadata comprises changing the first beat classification to a second beat classification for each beat in the set of beats.

5. The system of claim 1, wherein the automatically update occurs without interaction with the server.

6. The system of claim 1, further comprising:
the server comprising: a database, a processor, and a computer-readable medium having a set of computer-executable instructions embodied thereon, the set of instructions configured to be executed by the processor to cause the server to:
identify, using a machine learning model operated by the server, cardiac events within the ECG data,
associate the metadata with the ECG data, the metadata including a first set of indicators of cardiac event types,
store the metadata to the database of the server, and
transmit, to the remote computing system, strips of the ECG data and the associated metadata and the executable code.

7. The system of claim 6, wherein the set of instructions are configured to be executed by the processor to cause the server to: receive the updated metadata and replace the first set of indicators with the updated metadata in the database.

8. The system of claim 7, wherein the set of instructions are configured to be executed by the processor to cause the server to: generate a Holter report based, at least in part, on the ECG data and the updated metadata.

9. The system of claim 7, wherein the set of instructions are configured to be executed by the processor to cause the server to: train the machine learning model using the updated metadata.

10. A method to be executed on a remote computing system, the method comprising:
receiving, by the remote computing system, a first package of electrocardiogram (ECG) data, metadata associated with the ECG data, and executable code from a server;
generating, by an internet browser operating the executable code, a report simulation page including strips of the ECG data and a summary of patient data based on the ECG data and the metadata;
displaying the report simulation page in a user interface (UI) via the internet browser;
displaying a report build page in the UI, the report build page including the ECG data and the metadata;
modifying the metadata in the report build page by changing a classification associated with a set of beats contained in the ECG data; and
using the internet browser to operate the executable code to automatically update the report simulation page in response to the modifying the metadata.

11. The method of claim 10, wherein the classification is a cardiac event type.

12. The method of claim 10, wherein the classification is a beat classification.

13. The method of claim 10, wherein each beat contained in the ECG data is associated with a beat classification.

14. The method of claim 10, wherein the automatically updating occurs without interaction with the server.

15. A method comprising:
receiving, by a server, electrocardiogram (ECG) data generated by a remote monitoring device;
identifying, using a machine learning model operated by the server, beats and cardiac events within the ECG data;
generating and associating, by the machine learning model, beat classifications with the beats, the beat classifications being metadata;
generating and associating, by the machine learning model, event classifications with the cardiac events, the event classifications also being metadata;
storing the metadata to a database of the server;
transmitting, to a remote computing system, strips of the ECG data, the metadata, and executable code;
operating the executable code locally at the remote computing system to calculate modifications to the event classifications or the beat classifications in response to user-selected changes to the metadata at the remote computing system;
receiving, by the server from the remote computing system, updated metadata comprising the modifications to the event classifications or the beat classifications; and
replacing, in the database, the beat classifications and/or the event classifications with the updated metadata.

16. The method of claim 15, further comprising:
generating a Holter report based, at least in part, on the ECG data and the updated metadata.

17. The method of claim 15, further comprising:
training the machine learning model using the updated metadata.

18. The system of claim 1, wherein the remote computing system includes an internet browser, wherein the executable code is operated by the internet browser to cause the remote computing system to generate the report simulation page, display the report simulation page, display the report build page, modify the metadata, and automatically update the report simulation page.

19. The method of claim 10, wherein cache memory of the remote computing system is used to perform calculations for the automatically updating the report simulation page.

20. The method of claim 15, wherein the modifications to the event classifications or the beat classifications are calculated without interaction with the server.

* * * * *